US00PP10172P

United States Patent [19]

Twomey

[11] Patent Number: Plant 10,172

[45] Date of Patent: Jan. 6, 1998

[54] VARIETY OF GRANDIFLORA ROSE PLANT NAMED 'TWOANGEL'

[75] Inventor: Jerry Twomey, Leucadia, Calif.

[73] Assignee: DeVor Nurseries, Inc., Watsonville, Calif.

[21] Appl. No.: 414,535

[22] Filed: Mar. 31, 1995

(Under 37 CFR 1.47)

[51] Int. Cl.[6] ..... A01H 5/00

[52] U.S. Cl. ..... Plt./11

[58] Field of Search ..... Plt./11, 18, 19

[56] References Cited

U.S. PATENT DOCUMENTS

P.P. 7,901 7/1992 Twomey ..... Plt./18

*Primary Examiner*—Howard J. Locker

*Attorney, Agent, or Firm*—Christie, Parker & Hale, LLP

[57] ABSTRACT

A grandiflora rose variety producing multi-pink-toned flowers.

1 Drawing Sheet

SUMMARY OF THE INVENTION

The present invention relates to a new and distinct grandiflora rose variety which was originated by my crossing as seed and pollen parents, two varieties known as 'Gitte' (also know as 'Korita') and 'Twobe', U.S. Plant Pat. No. 7,901 (also known as 'Sheer Elegance'), respectively. The varietal denomination of this new rose is 'Twoangel'. Among the novel characteristics possessed by this new variety which distinguish it from its parents and all other varieties of which I am aware are its attractive multi-pink-toned flowers borne on a vigorous disease resistant plant. The color on the edging becomes a deep color while the remainder of the petal lightens.

Asexual reproduction by budding of the new variety as performed in Watsonville, Calif., shows that the foregoing and other distinguishing characteristics come true to form and are established and transmitted through succeeding propagations. Other known useful forms of asexual reproduction may be also employed.

Comparison With Parents

The variety 'Sheer Elegance' is a pink blend hybrid tea and 'Gitte' is a red-orange hybrid tea, whereas 'Twoangel' is a grandiflora producing flowers having more of an orange glow or cast to the multi-pink-toned flowers than does 'Sheer Elegance'. Flowers of 'Gitte' are much larger than the new variety and the new variety is more disease resistant than either of the parents.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—'Gitte'.

*Pollen parent.*—'Sheer Elegance'.

Class: Grandiflora.

The following is a detailed description of the new variety, from specimens grown outdoors in Watsonville, Calif., in the month of September. The color terminology used is in accordance with The Royal Horticultural Society Colour Chart (RHSCC), and refers to plate numbers in the aforementioned color chart. Phenotypic expression may vary depending on light, environmental and cultural conditions.

Flower

Blooming habit: Recurrent.

A. Bud:

(1) *Size.*—Medium.

(2) *Form.*—Pointed and tapering.

(3) *Color.*—When sepals first divide, bud color is near 48D.

(4) *Sepals.*—Longer than bud, about 3 cm to 4 cm long, spread and reflex when bloom opens; some sepals are foliaceous. Color: Near 137D on top surface, outer ¾ edge of sepal, center near 176A, under surface is slightly lighter with near 176A at margin.

(5) *Peduncle.*—Length: About 7 cm to about 9 cm. Aspect: Small prickles. Strength: Erect, sturdy. Color: Near 143C.

(6) *Bracts.*—Very few bracts, about 1 or 2; near 147A; about 5 cm to 6 cm below bud.

B. Bloom:

(1) *Size.*—Average size when fully expanded — about 8.5 cm to about 10 cm.

(2) *Borne.*—Singly.

(3) *Form.*—Balls slightly in center when about ½ open, imbricated when fully open. The term "balls" means that the center is covered by one or more petals and gives the affect of a ball at the center. This condition exists until the flower is about ½ open and as the flower opens further the center becomes visible.

(4) *Petalage.*—Number of petals under normal conditions — about 18 to 22.

(5) *Color (⅓ to ½ open).*—Outer petals — Top Surface: Top ⅛ edge near 52C; ¾ of petal near 37D; Undersurface: Bottom toward point of petal attachment of petal near 33D with upper, outer edge near 51B; middle of petal is near 36C; base of petal is near 150D. The foregoing reflects the description of the variety which is multi-pink-toned. Inner petals — Top surface: Upper, outer ¾ of petal is near 50D; base of petal is near 37D with bottom of base toward point of petal attachment being near 150D; Undersurface: Top ¼ to ⅓ of petal is near 48D; rest of petal is near 49A with some near 150D towards base of petal toward point of petal attachment. Base of petals — At point of attachment): Near 4B. General tonality from a distance — Multi-pink-toned.

(6) *Color (fully open).*—Outer petals — Top surface: Color on edges ranges from near 52C to 52B; middle of petal is near 36D; base of petal is near 155B; Undersurface: top edge of petal is near 51C; middle of petal is near 36D; base of petal is near 155C. Inner petals — Top surface: most of petal is near 49D with edge near 50D; Undersurface: most of petal is near 49D with edge near 51C. Base of petals — (At point of attachment): Near 4B. General tonality from a distance — Multi-pink-toned (7) *Color change.*—As bloom ages — Edges are deeper and more intense pink; opens to reveal center; middle of petals are lighter color. Petal top surface — Edges look deeper pink as middle lightens. Petal undersurface — Loses orange case and is more a light pink. General tonality at a distance — Multi-pink-toned.

Petals:

(1) *Texture.*—Thick, smooth.

(2) *Appearance.*—Inside slightly velvety; outside matte and somewhat satiny.

(3) *Form.*—Orbicular.

(4) *Arrangement.*—Imbricated.

(5) *Petaloids.*—Few.

(6) *Fragrance.*—Mild musk.

(7) *Lasting quality.*—Long lasting on plant, about 9 to 12 days, about 7 to 10 days after cutting.

(8) *Persistence.*—Petals drop off cleanly.

Reproductive Organs

A. Stamens:

(1) *Arrangement.*—Regularly arranged around styles, uneven.

(2) *Stamens.*—Near 163B to 163D.

(3) *Anthers.*—Color near 163B to 163D.

(4) *Filaments.*—Top near 35A, bottom near 12C.

(5) *Pollen.*—Color — near 163B to 163D.

B. Pistils:

(1) *Styles.*—Bunched, uneven, thin.

(2) *Stigmas.*—Color near 35A, tip near 161C, bottom near 12C.

C. Characteristics of hips: Hips have not been observed.

Plant

A. Form: Upright.

B. Growth: Very vigorous, about 4½ to 5 feet in the first season.

C. Foliage: Compound 3 to 5 leaflets, some compound 7 leaflets.

(1) *Size.*—Medium, similar to pellen parent.

(2) *Quantity.*—Abundant.

(3) *Color.*—New foliage — upper side near 147A edged with near 183A; underside near 148B; mature foliage — upper side near 137A, underside near 191B.

(4) *Shape.*—Ovate.

(5) *Texture.*—Upper side glossy, smooth; underside semi-leathery, matte.

(6) *Edge.*—Serrate.

(7) *Serration.*—Denticulate.

(8) *Leaf stem.*—Color — medium green.

(9) *Stipules.*—Adnate, parallel, glandular.

(10) *Rachis.*—Small prickles on underside

(11) *Petioles.*—Top near 146A, underside near 146C.

(12) *Auricle.*—Slender, small glands.

(13) *Resistance to disease.*—Very resistant to blackspot, mildew and rust.

D. Wood:

(1) *New wood.*—Color near 183A, bark smooth.

(2) *Old wood.*—Color near 147C, bark smooth.

E. Thorns:

*Quantity.*—On main stalk, average; few on laterals.

*Form.*—Slightly curved downward.

*Length.*—Medium.

*Color.*—When young near 184C at base and tip, with tinge of near 147C throughout.

*Position.*—Irregular.

*Prickles.*—Ordinary.

G. Winter hardiness: Winter hardy in Southern California.

I claim:

1. A new and distinct grandiflora rose plant variety, substantially as shown and described.

* * * * *

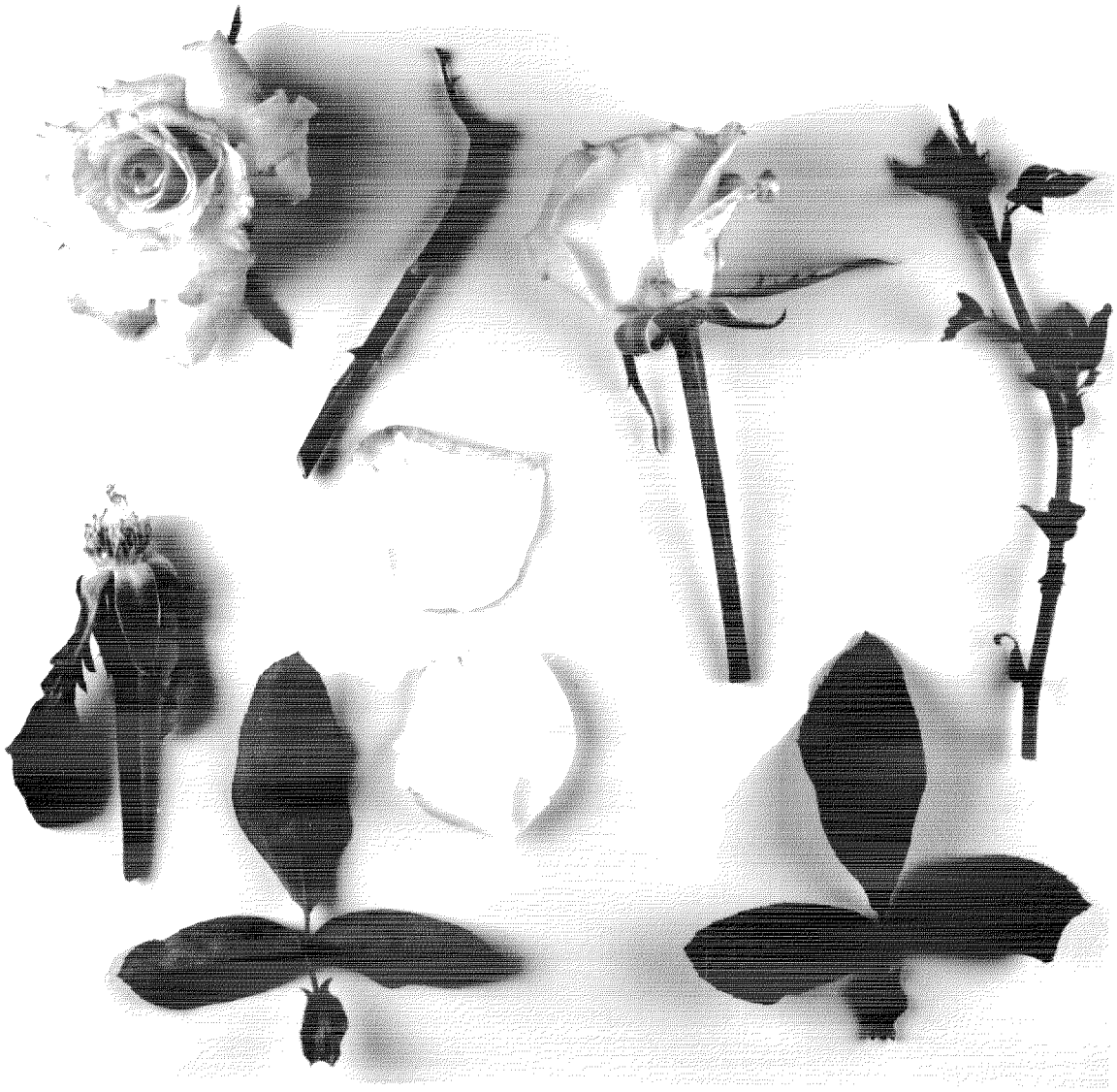

UNITED STATES PATENT AND TRADEMARK OFFICE

CERTIFICATE OF CORRECTION

PATENT NO. : Plant 10,172
DATED : January 6, 1998
INVENTOR(S) : Jerry Twomey

It is certified that error appears in the above-indentified patent and that said Letters Patent is hereby corrected as shown below:

Column 3, line 1, change "—At" to -- —(At --.
Column 3, line 17, replace "case" with -- cast --.
Column 4, line 7, replace "pellen" with -- pollen --.

Signed and Sealed this

First Day of December, 1998

*Attest:*

BRUCE LEHMAN

*Attesting Officer*

*Commissioner of Patents and Trademarks*